United States Patent [19]
Raviv

[11] Patent Number: 5,444,786
[45] Date of Patent: Aug. 22, 1995

[54] SNORING SUPPRESSION SYSTEM
[75] Inventor: Gil Raviv, Northbrook, Ill.
[73] Assignee: SNAP Laboratories L.L.C., Glenview, Ill.
[21] Appl. No.: 15,569
[22] Filed: Feb. 9, 1993
[51] Int. Cl.⁶ .............................................. G10K 11/16
[52] U.S. Cl. ...................................................... 381/71
[58] Field of Search ............................. 381/71, 72, 94

[56]  References Cited
U.S. PATENT DOCUMENTS

| | | | |
|---|---|---|---|
| 4,423,289 | 12/1983 | Swinbanks | 381/71 |
| 4,473,906 | 9/1984 | Warnaka et al. | |
| 4,654,871 | 3/1987 | Chaplin et al. | 381/72 |
| 4,677,676 | 6/1987 | Eriksson | |
| 5,133,017 | 6/1992 | Cain et al. | 381/71 |

FOREIGN PATENT DOCUMENTS 0465174  1/1992  European Pat. Off.
2091064  7/1982  United Kingdom.

Primary Examiner—Forester W. Isen
Attorney, Agent, or Firm—Welsh & Katz, Ltd.

[57]  ABSTRACT

An adaptive snoring signal suppression system globally cancels snoring signals by determining a canceling signal based on a received snoring signal. The system creates a doublet between a plane of a speaker and the source of the snoring signal such that at the plane of the speaker, the canceling signal is 180 degrees out of phase with the snoring signal as measured at the source. The system uses digital signal processing to adaptively estimate a snoring sound canceling signal based on past snoring signals.

20 Claims, 5 Drawing Sheets

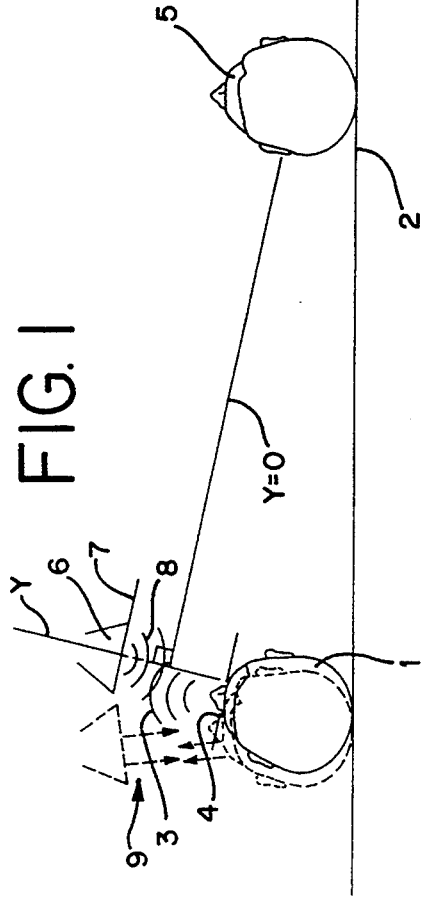
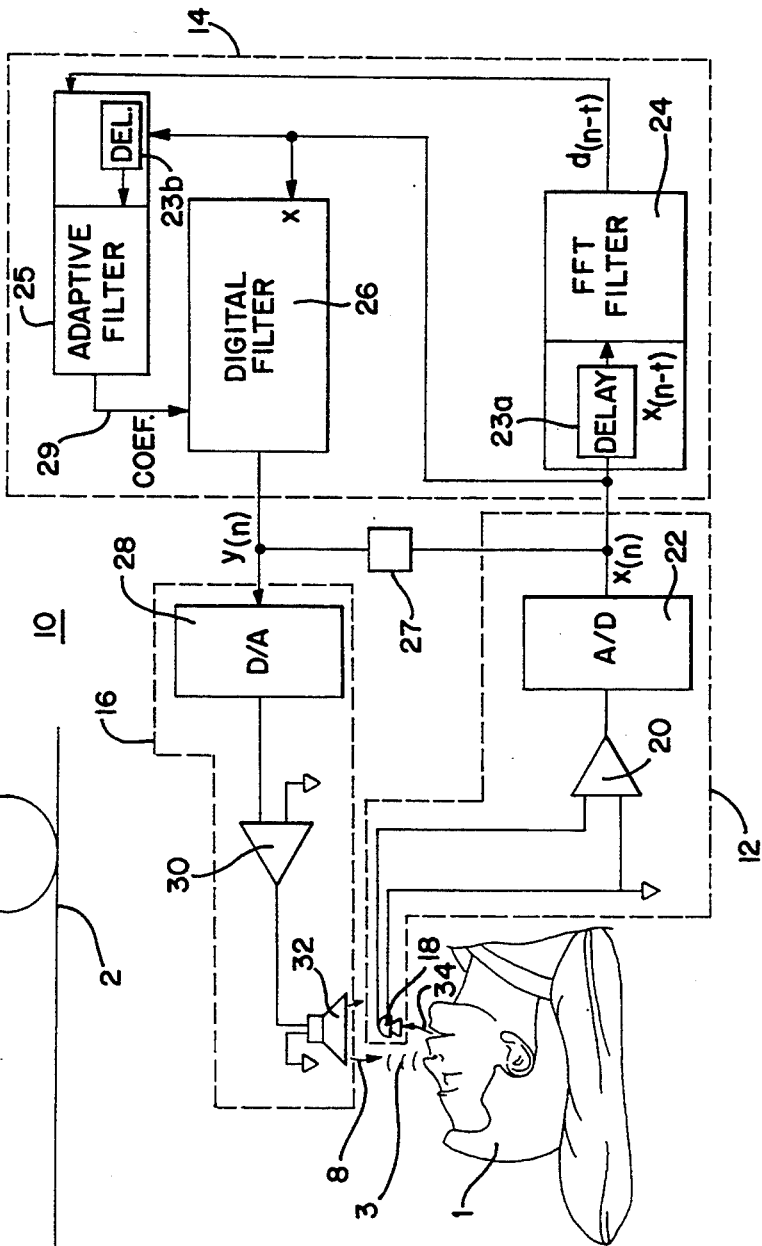
FIG. 1
FIG. 2

SNORING SUPPRESSION SYSTEM

BACKGROUND OF THE INVENTION

The invention relates generally to apparatus and systems for suppressing sounds resultant from snoring and more particularly to systems for suppressing sounds produced by snoring wherein the originating snoring sounds are substantially suppressed by generating sound canceling signals.

Many attempts have been made to overcome the problem of snoring for both the snoring person and other persons that may hear the snoring sounds. Many systems and methods for eliminating the problem of snoring are designed to awaken or otherwise interrupt the person generating the snoring sounds. For example, some systems activate an alarm based on a predetermined loudness level of the snore sensed by a sound sensor. Another system includes an eye cover which has an actuating mechanism for activating a flashing light so that the snorer is awakened upon sensing of snoring sounds. However, such systems unnecessarily wake up a snoring person so that the snoring person is deprived of a comfortable rest.

Other systems which have been developed in an attempt to overcome the problem of snoring include air bags which may be mounted to the back of the snoring person to prevent the person from lying on their back. This may prevent snoring, but may do so at the expense of comfort. Another system includes a sling which is worn over the mouth of a person to keep the mouth closed so that the wearer is unable to generate a snoring sound. These systems unnecessarily restrict the physical comfort of the snoring individual so that the snoring individual is forced to sleep in an unnatural state.

Other systems, such as ear plugs for the non-snoring person reduce the effects of snoring by attempting to completely block all sounds (particularly the snoring sound signal) from reaching an ear drum of the non-snoring person. This allows the snoring person to sleep comfortably and continue snoring. However, such systems are typically onerous and possibly life threatening to the non-snoring person since the non-snoring person might be unable to hear other audible signals, such as audible smoke alarm or fire alarm warning signals.

No snoring attenuation systems are known that substantially cancel or otherwise attenuate snoring sound signals so that neither the snoring person nor another non-snoring person needs to wear an overly restrictive or unnecessarily uncomfortable snore prevention system. Although the theory of sound cancellation through the use of canceling signals is generally known, no snoring sound signal attenuation systems are known that use audible canceling signals to suppress snoring sounds. In general, audible canceling signals typically have a same amplitude but a phase angle that is 180 degrees from that of a source sound signal.

Known adaptive sound cancellation systems, cancel sounds (noise) at a location other than the source of the sound, such as at an opening in a duct. Typically, the point at which a cancellation signal is directed (cancellation point) is fixed and down stream from the signal source. For example, many systems cancel sound at a point downstream from the source of a sound such as an opening in a duct so that the control system has adequate time to determine a proper cancel signal. Therefore, where the noise cancellation point is sufficiently distant from the source of the noise, and a sensor is placed at the source and another sensor at the cancellation point, the control system may readily calculate and output a canceling signal downstream from the source.

One example is disclosed in European Patent Application 465,174 entitled "Adaptive Active Noise Cancellation Apparatus". Such a system uses a control system to cancel noise at an opening of a duct. The control system uses an adaptive filter for aiding in reducing unwanted noise in ducts. However, such known noise cancellation systems typically require the use of a plurality of microphones for determining an error signal, and a duct for conducting sound (audible) signals so that the sound source signal is directionally limited to better facilitate cancellation.

Such systems, typically determine the error signal by placing a microphone at the opening of the duct to determine the level of noise emanating from the opening of the duct. Such an error signal may then be input into an adaptive filter after being delayed by a predetermined time. A second microphone or sensor is typically placed at the source of the noise to determine the actual source sound signal. The adaptive filter uses the error signal to determine a canceling signal, having the same amplitude but a 180 degree phase difference from the error signal emanating at the opening of the duct. The output signal is typically output by a signal processor through a speaker directed at the duct opening to substantially cancel the sound signal at the opening.

However, such systems are typically limited to reducing noise signals at a single stationary point (duct opening) away from the source. Canceling signals away from the source gives these types of systems ample time to generate and evaluate error signals to better calculate canceling signals. In addition, such duct-type systems are typically not adapted to operate in an open area, such as a bed room or other room in a house. Such open areas may allow the source signal to radiate and propagate in many directions unlike the duct arrangement which guides the signals to an opening. Furthermore, such duct systems require at least two sensors, one for sensing the source sound signal and one for sensing the signal at the duct opening to determine an error signal. Also, since the duct opening is typically the only point at which noise may be radiated, the control system attempts to calculate and output a canceling signal so that the canceling signal plane of the duct opening is 180 degrees out of phase with respect to the noise signal at the plane of the duct opening.

Another known noise attenuation system, such as that disclosed in U.S. Pat. No. 4,677,676 entitled "Active Attenuation System With On-line Modeling of Speaker, Air Path and Feedback Path", also utilizes a duct arrangement. Again, such systems do not cancel at the source of the sound signal and use an additional microphone located down stream from where the canceling signal is output, to determine an error signal.

Based on the foregoing, known noise canceling systems typically cancel at a fixed, nonmoving point, such as an opening in a duct. Therefore, known noise canceling systems are typically not suitable wherein the sound to be canceled is a moving sound source such as a snoring sound source.

A problem also arises with such systems where a source may emanate in a substantially omnidirectional pattern. Such is the case with a snoring individual since snoring sounds are typically emanated in almost an omnidirectional pattern in an open room. Furthermore, it would be desirable to substantially globally cancel snoring sounds instead of attempting to locally cancel a sound at a selected point away from the source since the snoring sound may be heard at points other than one fixed point. Global reduction of the snoring sound would also be advantageous since an individual (the ears of the individual), such as a non-snoring spouse, may move throughout the night.

SUMMARY OF THE INVENTION

Accordingly, it is an object of the invention to provide a snoring attenuation system that substantially facilitates global suppression of snoring sound signals.

It is another object of the invention to provide a snoring attenuation system that substantially facilitates global suppression of snoring sound signals by creating a doublet between a canceling sound output device, such as a speaker, and the snore signal source, such as a mouth of a snoring person wherein the canceling sound output device produces a snore cancel signal to cancel at least some of the snore sound signal.

It is also another object of the present invention to provide a snoring attenuation system that facilitates the suppression of snoring sounds substantially at the source of the snoring sound signals wherein the source may move during output of the snore signal.

It is an object of the present invention to provide a snoring attenuation system that allows the snoring person to sleep in a comfortable position and without unnecessary interruption.

It is yet a further object of the present invention to provide a snoring attenuation system that facilitates suppression of snoring sounds substantially at the source of the snoring sound signal wherein the system includes a tracking mechanism for determining the location of the snoring sound source signals to facilitate snore sound cancellation for a moving snore signal source.

It is also an object of the present invention to provide a snoring attenuation system that may prevent the output of canceling signals in response to an evaluation of a snore source signal.

It is another object of the present invention to provide a snoring attenuation system that facilitates the suppression of snoring sounds by outputting a snore cancellation signal from at least one of a plurality of speakers wherein the plurality of speakers are selectively activated in response to the sensed location of the snoring sound source.

It is a further object of the invention to provide a snoring attenuation system that substantially facilitates global suppression of snoring sound signals by creating a doublet between a canceling sound output device, such as a speaker, and the snore signal source, such as a mouth of a snoring person, wherein the system includes an adaptive filtering mechanism for determining and generating a snore canceling signal based on an analysis of a current snore signal.

A snoring suppression system is disclosed which includes a sound receiving stage such as a cordless microphone coupled to an A/D circuit. The microphone may be located in a mouth piece placed in the mouth of the snoring person. A sound transducing device, such as speaker, outputs a snore canceling signal toward the snoring sound source to form a doublet between the sound transducing device and the snore sound source. A signal processor generates the snore canceling signal based on the received snore signal, such that the snore canceling signal, as measured at a plane of emission of the sound transducing device, has approximately an 180 degree phase difference from the snoring signal phase angle and a substantially same amplitude as the snoring signal amplitude as measured at the snore source or the mouth of snoring person. The system may include a sensing mechanism for determining a position of the snore sound source during movement of the snore sound source.

The system may also include a transducer control mechanism for preventing the canceling signal from being output by the transducing device when the snoring signal, as received by the receiving means, does not conform to some type of predetermined signal criteria, such as average signal strength or signal correlation parameters.

The sensing mechanism may include a position sensing mechanism, such as an ultrasonic emitter and detector pair, wherein one of either the emitter or detector may be suitably affixed to the snore sound source, such as affixed in a mouthpiece, and the other component may be suitably affixed to the transducing device. The sensing mechanism may then determine the location of the snore sound source. The position sensing mechanism has a controller for activating or deactivating the transducing device in response to an output signal from the position sensor.

For example, the system may include a multi-speaker select mechanism to selectively activate at least one of a plurality of speakers in response to the output signal from the position sensing mechanism so that an optimum speaker from the plurality of speakers may be selectively activated to effectuate suitable snore signal suppression. The system may also include a movable transducing device. The sensing mechanism may be used to facilitate movement of a speaker coincident with a moving sound source to maintain a relative position between the sound transducing device and the snore sound to effectuate suitable snore signal suppression.

The digital signal processing stage is adapted to receive a digital signal representation of the received snore signal and determines a plurality of filter coefficients. The signal processing stage modifies the digital signal representation of the snore signal using the coefficients to generate a pre-output canceling signal wherein the pre-output canceling signal becomes the canceling signal output by the transducing device. The digital signal processing stage further includes a filter, such as a fast Fourier transform (FFT) filter, for outputting the digital signal representation in a plurality of frequency ranges.

In another embodiment, a second microphone may be positioned to evaluate and adjust the suppressing effect of the system. For example, the microphone may be located in a headset worn by an adjacent person to determine the signal heard by the adjacent person. The system may then adjust the canceling signal to optimize suppression of the snore signal.

A method is disclosed which includes receiving the snoring sound signal proximate the snore sound source; outputting a snore canceling signal directionally toward the snoring sound source to form the doublet between the speaker and the snore sound source; generating the snore canceling signal, such that the snore canceling signal, as measured at a plane of emission of the speaker, has approximately an 180 degree phase difference from the snoring signal phase angle and a substantially same amplitude as the snoring signal amplitude as measured at the source of the snore signal.

The method may further include the steps of determining a position of the snore sound source during movement of the snore sound source; and preventing the canceling signal from being output by the speaker when the snoring signal is not within the predetermined signal criteria.

BRIEF DESCRIPTION OF THE DRAWINGS

FIG. 1 is a pictorial representation generally illustrating a doublet formation between a plane of a speaker and a snoring sound source to globally reducing snoring signals in accordance with the invention;

FIG. 2 schematically depicts a snoring suppression system in accordance with the invention;

FIG. 3b is an alternative embodiment to the diagram shown in FIG. 3a;

FIG. 4b is a block diagram generally depicting a system for controlling the multi-speaker system shown in FIG. 4a;

DETAILED DESCRIPTION OF THE PREFERRED EMBODIMENTS

Figure 3A:
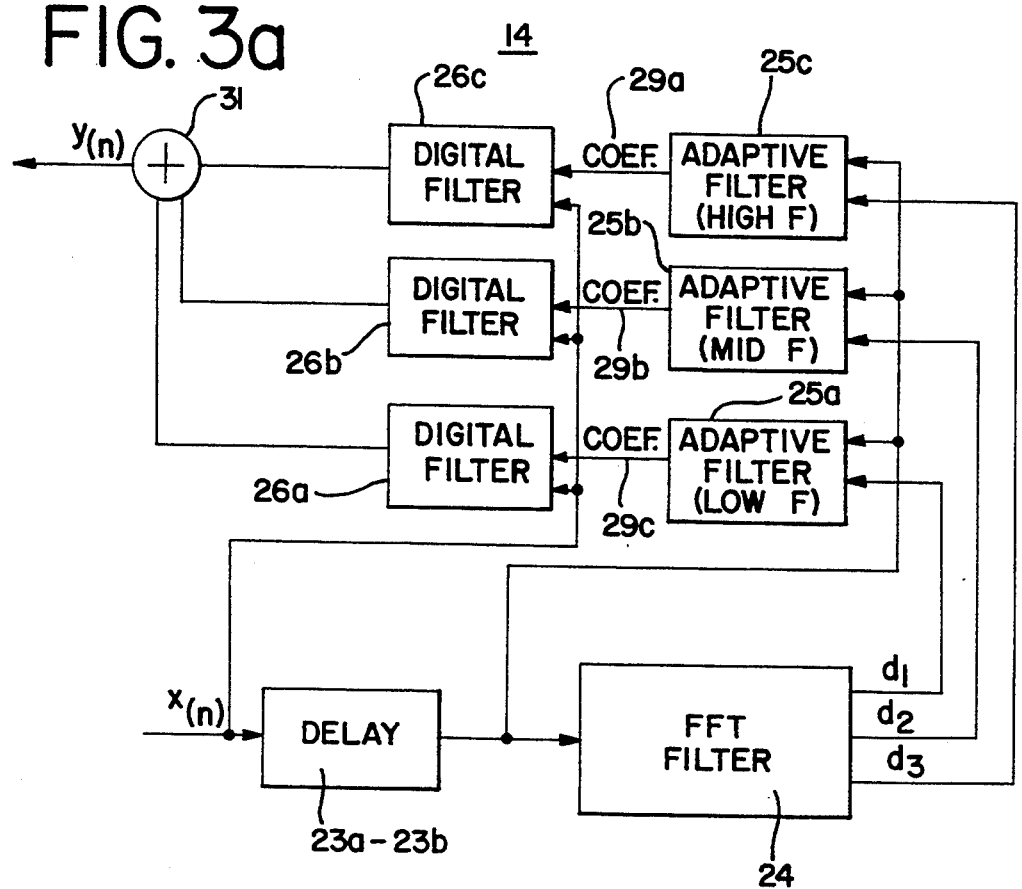
FIG. 3a is a block diagram generally depicting one embodiment of a snore cancel signal generating stage for use in the system shown in FIG. 2.

FIG. 1 generally illustrates the creation of a doublet as created by the inventive snoring attenuation system for globally reducing snoring signals. As shown, a snoring person 1 laying on a bed 2 emits a snore source signal 3 from a snore source 4, such as a snorer's mouth. The snore source signal 3 has an amplitude, frequency and phase angle associated with it. An adjacent person 5 is assumed to be in hearing range of the snore source signal 3.

A cancel signal output device 6, such as a speaker, has a plane 7 and emits a snore canceling signal 8 in an opposing direction, along the Y-plane, to that of the snore source signal 3. The snore canceling signal 8 as output at the plane 7 of the speaker, has a substantially same amplitude and frequency, but a phase difference of 180 degrees compared to the snore source signal measured at the mouth 4 of the snoring person 1.

When the speaker 6 and the snore source 4 are close enough to each other, a sound source doublet is created between the speaker 6 and the snore sound source 4 (mouth) so that the snore sound is substantially suppressed. The best snore suppression occurs along a Y=O plane wherein O is a point located midway along a Y-axis between the snore source 4 and the plane 7 of the speaker and at 90 degrees with respect to the Y-axis. Therefore the other person 5, when positioned as indicated, hears less snoring noise due to the canceling of the snore sound. As shown by the dashed lines 9, the snore source 4 may move as the snoring person 1 turns their head, thereby changing the location and orientation of the Y-axis. Consequently it is desirable to move the speaker 6 to maintain a doublet that cancels signals in the plane(s) coincident with the other persons ear. It will be recognized that some form of signal attenuation occurs in planes on either side of the Y=O plane. Consequently, the system provides suppression of snoring signals at more than one point, hence the term global suppression.

FIG. 2 schematically depicts a snoring attenuation system 10 in accordance with the invention to carry out the doublet effect as generally described above. The system 10 includes a snore sound signal receiving stage 12, a snore canceling signal generating stage 14, formed from a digital signal processor, which receives a current digital snore sound signal x(n) from the receiving stage 12, and a sound transducing stage 16 for outputting a snore canceling signal as generated by the canceling signal generating stage 14.

The snore signal receiving stage 12 may include a microphone 18 positioned adjacent to or in the mouth of a snoring person 1. An amplifier 20 receives the snore source signal 3 from the microphone 18 and amplifies it to a suitable level as known in the art. An output from the amplifier 20 is converted from an analog signal to a digital signal x(n) through A/D converter 22.

The snore canceling signal generating stage 14 includes a fast Fourier transformation (FFT) filter stage 24, an adaptive filter stage 25 and a digital filter stage 26. A plurality of delay stages 23a and 23b represent the delay incurred in accumulating signal samples for the FFT filter stage 24 and the adaptive filter stage 25; both of which do not process signals in real time.

The digitized snore signal x(n) also serves as an input to the digital filter stage 26 and a speaker control stage 27 as will be described later. The FFT filter stage 24 receives the digitized snore signal x(n) and accumulates signal samples to carry out an inverse operation using the inverse transfer function of the system 10 (which take into account the distortion and delays from the various components in system) as known in the art.

In general, the FFT filter stage 24 and the adaptive filter stage 25 facilitate the determination of fixed (although periodically changed) filter coefficients 29 for the digital filter stage 26. In order to calculate the filter coefficients 29, an assumption is made that the statistics of the snoring signal will be relatively constant over a predetermined period of time (e.g. 50 msec, 500 msec or 1000 msec) so that the fixed coefficients 29 will remain "fixed" for some predetermined period of time but that the coefficients 29 may change from one time interval to another in response to the varying snore signal x(n).

The FFT stage 24 includes an FFT processing stage, a multiplication mechanism, and an inverse FFT processing stage. The FFT processing stage converts temporal signal data to frequency domain data. The output from the FFT processing stage serves an input to the multiplication mechanism. The multiplication mechanism modifies the output frequency domain signal data by multiplying the frequency domain data by matrix elements that represent the inverse transfer function of the system 10. The output from the multiplication mechanism serves as the input to the inverse FFT processing stage. The inverse FFT processing stage generates a desired output signal d(n-t). However, it will be recognized that any suitable signal processing technique may also be used instead of the FFT stage 24, such as a series of digital filters.

The desired output signal d(n-t) represents a canceling signal that would have canceled a delayed snore signal x(n-t). The desired output signal d(n-t) serves as an input to the adaptive filter stage 25. The adaptive filter stage 25 determines the filter coefficients 29 necessary to generate the proper canceling signal y(n-t) for x(n-t). The digital filter applies the coefficients to the snore signal x(n).

The adaptive filter 25 utilizes the desired cancel signal d(n-t) and the delay signal x(n-t) to determine the coefficients required to generate d(n-t) from x(n-t). The digital filter 26 receives the digitized snoring signal x(n) and modifies the snoring signal x(n) in real time by the fixed filter coefficients 29 to produce the corresponding pre-output canceling signal y(n). The pre-output cancel signal y(n), derived from x(n), corresponds to the signal which, when passed through the stage 16, becomes the canceling signal 8. Since the system 10 has internal delays $\tau$, the cancel signal generating stage 14 predicts the snore signal at time $\tau$ after a given sample is taken and generates a corresponding snore cancel signal 8. The cancel signal generating stage 14 uses current and previous snore signal samples to generate the cancel signal 8. It is assumed that the snore signals are predictable for a period of time equal to the delay $\tau$ in the system 10.

The sound transducing stage 16 converts the generated pre-output canceling signal y(n) to an analog signal through the digital to analog converter 28. The output from the D/A converter 28, is amplified through amplifier 30. The output from amplifier 30 serves as the input to the sound transducer 32, such as a speaker 8 (shown in FIG. 1).

The speaker controller stage 27 may be a microprocessor or a portion of the digital signal processor that forms the canceling signal generating stage 14 and serves to detect an uncorrelated signal or otherwise anomalous signal. The speaker controller stage 27 prevents the sound transducer 32 from outputting audible sounds in response to predetermined signal criteria such as the detection of an undesirable condition. For example, where the average amplitude of a snore signal rises or falls below a predetermined threshold, audible output to the sound transducer 32 may be prevented. Such a condition may arise when unexpected noises are detected and can not be canceled until enough samples are obtained by the FFT and adaptive filters.

Also, the speaker controller 27 may prevent signals from being output if the snore signal and the canceling signal fail to converge after a predetermined time. The speaker controller 27 may also prevent the output stage 16 from outputting a signal if a runaway signal is detected, such as if x(n) is an undesirable resonating signal. It will be recognized that any suitable signal analysis technique may be used such as logarithmic correlation techniques or average amplitude sampling techniques. Also, the speaker controller 27 may be connected to other control systems such as the detection mechanism described with reference to FIG. 4b or may be incorporated as part of the detection mechanism.

Other criteria may also serve as the basis for prohibiting a cancel signal from being output. For example, the adaptive filter 25 may determine that it is unstable and cease to output coefficients 29. In this case, the digital filter 26 may continue to use prior coefficients which in turn would affect the pre-output cancel signal. The speaker controller 27 may then determine that the cancel signal and the snoring signal do not converge and subsequently prohibit the cancel signal from being output. Alternatively, the adaptive filter 25 may directly prohibit signal output to the speaker.

FIG. 3a depicts generally a preferred embodiment for the canceling signal generating stage 14. It has been found that low frequency snoring signals typically have few harmonics. Consequently, lower frequency signals such as those between the range of approximately 20 Hz to 120 Hz, allow the digital signal processing to be simplified so that fewer samples may be taken and analyzed to generate a proper fixed coefficient and suitable canceling signal. More particularly, the FFT may use a small portion of the transfer function matrix, as known in the art, which reduces the complexity of the signal processing.

The FFT filter stage 24 divides the samples of the current digital signal x(n) into a plurality of sample sets corresponding to different frequency ranges. For example, signal portion d1 may include signals in the range of 20-250 Hz, signal portion d2 may include signals in the range of 250-450 Hz and signal portion d3 may include signals in the range of 450-1000 Hz.

Each of the adaptive filters 25a–25c may include a prefilter portion which includes a constant delay filtering section to filter out the frequencies of non-interest from x(n). For example, adaptive filter 25a may have a low pass filter to allow the low frequency component of x(n) to be analyzed. A sampling rate divider portion in each of the adaptive filters 26a–26c allows each respective filter to sample the input signal to each of the filters at a selected rate. For example, since lower frequencies need not be sampled as often to obtain sufficient information for the signal, the adaptive filter 25a may sample one out of every eighth signal element. Similarly, adaptive filter 25c may sample every signal element since more samples are generally required to analyze higher frequency signals.

Each of a plurality of adaptive filters 25a–25c are configured to calculate filter coefficients 29a, 29b and 29c for one of the frequency ranges. For example adaptive filter 25a may be configured to calculate coefficients for low frequency ranges (20 Hz–250 Hz) whereas adaptive filter 25c may be configured to calculate coefficients for the high frequency ranges (450–1000 Hz). Each adaptive filter 25a–25c provides the coefficients 29a–29c for a corresponding digital filter 26a–26c. The adaptive filters 25a–25c may employ a least means squares technique, or a recursive least squares RLS technique, however, any other suitable filtering technique may also be used.

Digital filters 26a–26c may include a plurality of identical sampling rate divider sections to facilitate proper signal sampling of x(n). For example, digital filter 26a may have eight identical digital filters in parallel wherein one digital filter samples a first signal element, a second digital filter samples a second signal element, a third digital filter samples a third signal element, etc. Each of the separate digital filters uses the same coefficient as received from the adaptive filter section 25a.

The output signal from each of the digital filters 26a–26c is combined through a summing circuit 31. The output from the summing circuit 31 serves as the generated canceling signal y(n) to the sound transducing stage 16 (see FIG. 2).

The system 10 may also include temporarily stored filter coefficients for use with different sections of the snoring signal to speed up the processing time for generating a pre-output cancel signal. For example, the frequencies during inhaling may have corresponding filter coefficients stored for initial use by the digital filters 26a–26c, whereafter the coefficients may be updated. Similarly, frequencies corresponding to exhaling may also have corresponding coefficients stored for initial use by the digital filters 26a–26c so that when the system detects exhaling signals, the system may initially use the stored coefficients for the signal processing steps to generate a suitable cancellation signal.

Figure 3B:
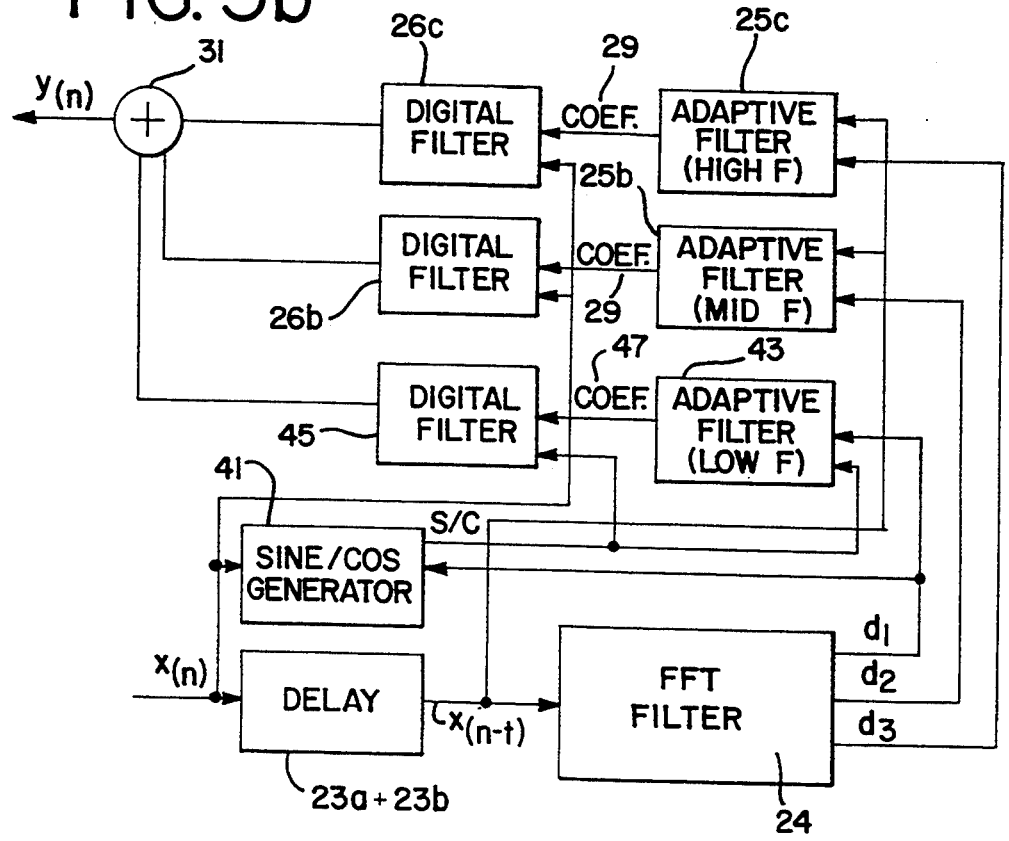

FIG. 3b is another embodiment of a canceled signal generating stage that may be applicable where the speaker has a high amount of distortion at low frequencies. FIG. 3b differs from FIG. 3a in that a sine/cosine generator 41 is used to represent low frequency components of the signal x(n) for adaptive filter 43 and a digital filter 45. The sine/cosine generator 41 modifies the signal x(n) for low frequencies as determined by an input signal portion f1. The input signal portion f1 is a series of frequencies from the FFT stage 24 which form the low frequency components of x(n) and is therefore indicated as being in the frequency domain.

The sine/cosine generator 41 produces sine and cosine waveforms that when combined form low frequency components of x(n). The sine/cosine generator 41 generates sine and cosine waveforms which are Eigen-functions of the system and may provide phase compensation and amplitude compensation for each sine and cosine representation as known in the art. The approach uses the fact that there are dominant frequencies and can extrapolate future signals using the sine and cosine signals.

The adaptive filter 43 generates new coefficients 47 which represent the contribution of each of the given frequencies that form the low frequency component of x(n). The digital filter 45 applies the coefficients 47 to the sine/cosine signals output by the sine/cosine generator 41 thereby recreating low frequency components of x(n). The digital filter 45 output is input to the summing circuit 31, as previously described. The system as shown in FIG. 3b allows the system to overcome and compensate for the high distortions at low frequencies. It will be recognized that although the above embodiment uses a single sine/cosine generator 41 for the low frequency portion of x(n), it may be advantageous to represent x(n) entirely in the form of sine and cosine components for all frequencies of x(n).

Referring to FIGS. 2–3b, the system 10 generates a canceling signal such that the canceling signal as measured at the plane of emission of the cancel signal 8 as output by the sound transducer 32 has a substantially same amplitude and frequency, but a phase difference of 180 degrees compared to the snore source signal measured at the mouth 4 of the snoring person 1 (see FIG. 1). It is preferred that the speaker 32 has a limited frequency response such as from 20 Hz to 1000 Hz which is the typical range of snoring sound frequencies. The speaker 32 may also be designed so that its response function approximates a minimum delay that is as constant as possible over a frequency range of the snoring signals (20 Hz–1000 Hz). However, any suitable speaker may be used.

The microphone 18 may be of the type which has rapidly decreasing sensitivity in proportion to its distance from the snore source signal. For example, the microphone 18 should not pick up the source sound signal if the microphone is moved too far away from a mouth of a snoring person 20. Since the speaker should be further from the mouth than the microphone, the effect of the output from the speaker will be minimized. This helps reduce the probability of feedback from the speaker.

A shield may also be secured about the microphone 18 to reduce the probability of feedback. In addition, the digital signal processing stage 14 may reduce undesirable resonance effects by detecting zero crossings of high amplitude components to initially detect a resonance problem and then suppress those resonant frequencies. For example, the FFT stage 24 may selectively use the inverse transfer function matrix to suppress the resonant components of the signal that represents the undesirable resonance.

Although not specifically shown in FIG. 2, the microphone 18 may be placed in a mouth guard, such as a plastic mouthpiece (also not shown), which may be worn by the snoring person 1. The microphone 18 may be a cordless microphone as known in the art so that the mouth piece and microphone combination is not uncomfortable or unnecessarily restrictive for the snoring person 1.

The snoring attenuation system 10 produces a doublet between the signal emission plane of the speaker 32 and the mouth 34 of the snoring person. Hence, a non-snoring person, such as a spouse lying next to the snoring person 1, will hear a suppressed snoring sound since the snoring sound is canceled at an angle of approximately 90 degrees with respect to the direction or angle between the speaker 32 and the mouth of the snoring person. It is preferred that the speaker 32 is positioned in an opposing direction to that of the snore source signal generator. Typically, the microphone 18 should be no more than approximately 2 centimeters away from the mouth of the snoring person 20 and the speaker 32 should be no more than approximately 40 centimeters from the mouth of the snoring individual 1. A preferred speaker distance is approximately 5–10 cm.

Figure 4A:
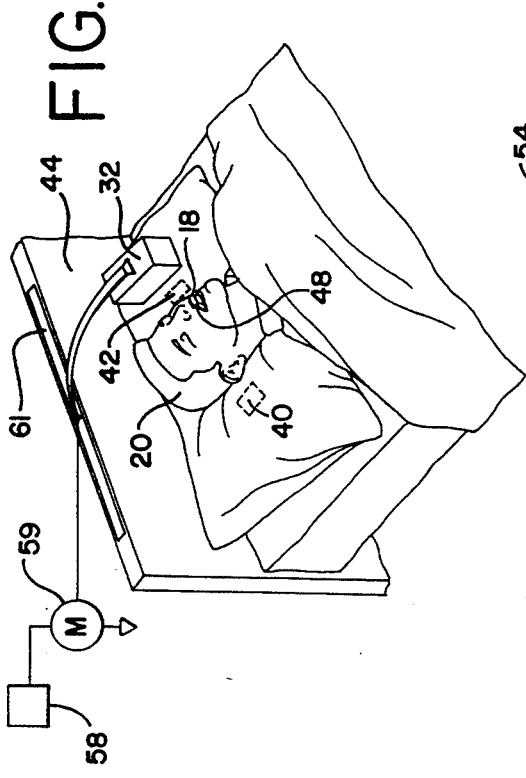
FIG. 4a is a perspective view of a multi-speaker snore reducing system in accordance with another embodiment of the invention.

FIG. 4a pictorially represents another embodiment of the invention that includes a plurality of speakers 32, 40, and 42 which may be selectively activated to output a snore canceling signal depending upon the head orientation or mouth location of the snoring person 1. As shown, the speaker 32 may be mounted to a headboard 44 or other suitable mount, so that one speaker may be positioned above the head to effectively minimize the distance between the cancel speaker and the snore signal source and to provide a 90° cancellation plane angle with the ears of the adjacent non-snoring person. Speakers 40 and 42 may be located on either side of the snorer's head in a pillow. However, the speaker 40 and 42 may also be suitably mounted to the headboard or otherwise resting on the bed at a distance which allows the snoring individual to uninhibitedly rotate the head.

Figure 4B:
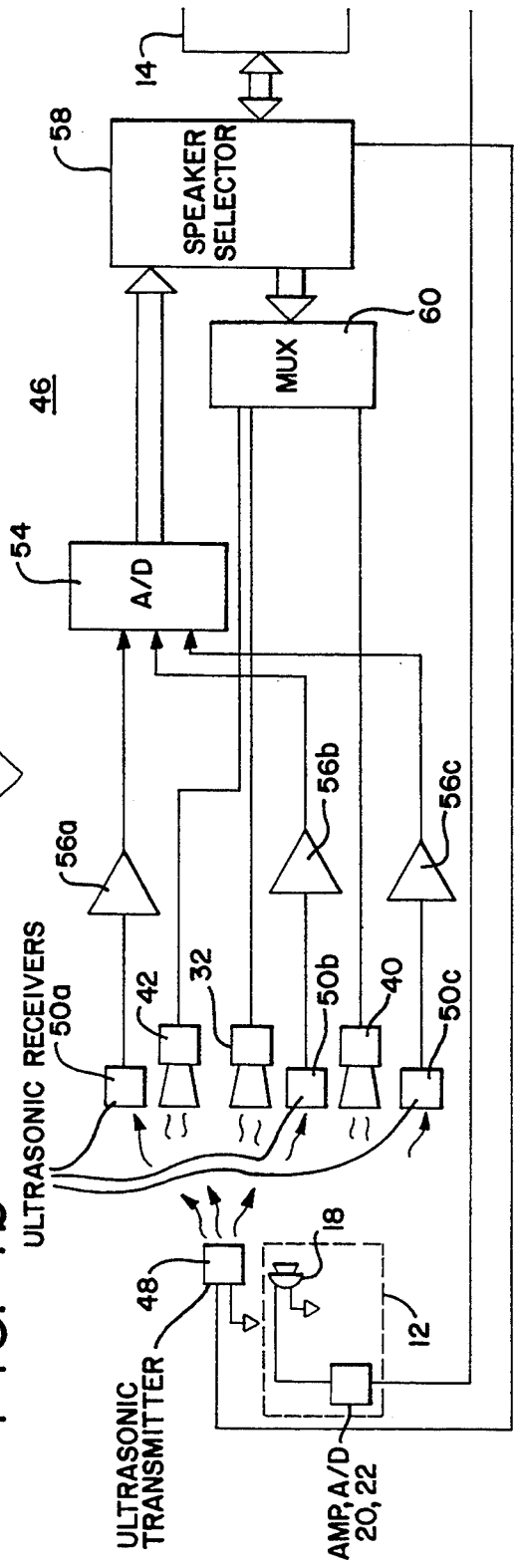

FIG. 4b is a schematic representation of a snoring attenuation system 46 as shown in FIG. 4a. The system 46 determines a location of the snoring source. The system 46 tracks the location or position of the snoring source signal using sensors. The system actuates one of the speakers to optimize cancellation of the snoring sound signal through ultrasonic sensors or other inaudible sensing mechanism. An ultrasonic transmitter 48 may be placed in the mouth piece worn by the person 20 or on the microphone 18 and transmits a pulsating or continuous ultrasonic signal. An ultrasonic sensor will not be heard by the snoring person nor the non-snoring persons. Ultrasonic receivers 50a, 50b and 50c, are located in a corresponding speaker 42, 32 and 40, respectively. The ultrasonic receivers 50a-50c are connected to an A/D converter 54 through amplifiers 56a, 56b and 56c. The ultrasonic receivers 50a-50c are suitably located in the speakers to detect the ultrasonic signal from the ultrasonic source 48.

A speaker selector 58 receives the detected ultrasonic signal and determines which ultrasonic receiver 50a-50c is receiving the strongest signal and may also determine the elapsed time for an emitted signal to be received by a detector to determine the distance between a selected speaker and the snore source. The speaker selector 58 is connected to a multiplexer 60 which activates the proper speaker 42, 32 or 40, via control from the speaker selector 58. The speaker selector 58 may also include the D/A function and amplification function of D/A 28 and amplifier 30 shown in FIG. 2. Furthermore, the speaker selector 58 may include the control functions of speaker controller 27, also as described with reference to FIG. 2.

For example, if ultrasonic receiver 50a which is located in speaker 42 receives the strongest ultrasonic signal from ultrasonic generator 48, the speaker controller 58, may then turn off speakers 32 and 40 so that the canceling signal is output by speaker 42. The speaker controller may also evaluate the elapsed time between a signal transmission from a transmitter and the detection by a corresponding receiver to evaluate the distance between the snore source and the speaker and turn on a speaker that is closer to the snore source although that speaker may not be receiving the strongest ultrasonic signal.

The ultrasonic sensors 50a-50c in effect determine which speaker is closest and/or has the best directional position to the source snore sound signal. As shown, the canceling signal generating stage 14 is coupled to the speaker controller 58 so that a suitable canceling signal may be multiplexed to the proper speaker.

Selective control of multiple canceling signal output devices as shown in FIGS. 4a and 4b, allow a snoring individual to continue snoring while the system determines the direction from which the strongest snoring signal is generated and/or the closest speaker to the snore source and selects the appropriate speaker from which the canceling signal is output. This offers substantially unrestrictive movement for the snoring individual and does not require an adjacent non-snoring individual to wear a restrictive snoring suppression system. It will be recognized that other suitable inaudible sensing systems may be used such as infrared sensors or the like which will not disturb either the snoring individual or non-snoring person.

The speaker controller 58 may be a suitable microcomputer containing software to determine which speaker is receiving the strongest signal. The speaker controller 58 may also be adapted to turn the speakers 42, 32 and 40 off or otherwise prevent a canceling output signal from being communicated to the speakers 42, 32 and 40. For example, a canceling signal may not be output when the sensors 50a-50c receive a signal having a level below a predetermined threshold or the elapsed detection time by an ultrasonic pair is too long (as described with reference to the controller 27 in FIG. 2). This may indicate that the snoring individual is too far from the speakers 50a-50c so that the canceling signal should not be output. Such a shut down mode avoids the cumulative affect of reducing snoring sounds being output from the speakers when such signals would not efficiently cancel a snoring signal. For example, if the speaker is too far away from the snoring signal source, and not in a substantially 180 degree phase difference and same amplitude at a point close enough to the source, canceling will not occur and the canceling signal will effectively add to the snoring signal and compound the snoring problem.

The speakers 32, 42 and 40 may each have a different frequency response range to facilitate varying canceling snoring signal outputs. For example, one speaker may have a frequency range of 20 Hz to 300 Hz, another speaker may have a frequency range of between 300 Hz and 500 Hz and a third speaker may have a frequency range of between 500 Hz and 1000 Hz. Such a system may be advantageous where the frequency response delay for one speaker over a certain range of frequencies is different from that of another one of the speakers. For example, where a speaker has a substantially constant delay over a frequency range of 20 Hz to 300 Hz, it may be advantageous to utilize that speaker for similarly ranged snore signal cancellation. Whereas it may be advantageous to use another speaker having a same delay over a different frequency response thereby reducing the processing time required by the digital filter 24.

Since low frequency speakers tend to be larger in size and given the nature of the omnidirectional sound at the low frequencies, the large speakers may be placed further away from the source. In contrast, it may be preferable to position high frequency speakers (smaller speakers) closer to the snore signal source.

In another embodiment, a single movable speaker may be employed with a sensing mechanism as previously described so that a speaker such as 32 may move in corresponding position with the mouth of a snoring individual. A drive motor 59 may receive a drive signal from the position sensing mechanism such as the speaker selector 58 to move the speaker to a suitable location. It will be recognized that the movable speaker 32 may be mounted on a slide rail 61 or other suitable mount and may be secured to a bed frame or other housing which facilitates movement of the speaker far enough above the individuals head so that the snoring individual is not unduly restricted.

It has been found that a difficult part in global cancellation of a point source in an open area is that physical systems have built-in delays throughout. For example, the speaker may have a delay associated with it which may vary over the frequency range of the speaker. Such a delay may result in a 0.2 to a 1 millisecond delay. Also, at low frequencies, the speaker may output a canceling signal that may be ahead in phase which must be taken into account by the output signal generating stage 14. Another example may be the microphone 18 and amplifier 20, each of which also have a delay associated with them. The doublet mechanism requires that a canceling signal (the output from the speaker) will be close to the snoring source (5 to 40 cm). In addition, any delay will cause the canceling signals not to cancel and in some cases may even strengthen the snoring signal by adding with the snoring signal if sufficient signal phase discrepancies are encountered (such as may occur at high frequencies).

Consequently, to avoid such drawbacks, the aforedescribed system "predicts" the cancellation signal so that the cancellation signal is output (as measured at the plane of the speaker) at a moment in time which is synchronized and without delay with respect to the snore source signal emitted from the snore source. Therefore the system as described above finds particular application where the snore signal is a stochastic signal. Based on the foregoing description, it will be evident that the system 10 globally suppresses the snore source signal proximate the source by creating a doublet between the cancel signal as measured at the plane of the speaker and snore signal source (at the mouth or received by the microphone in the mouth).

Figure 5:
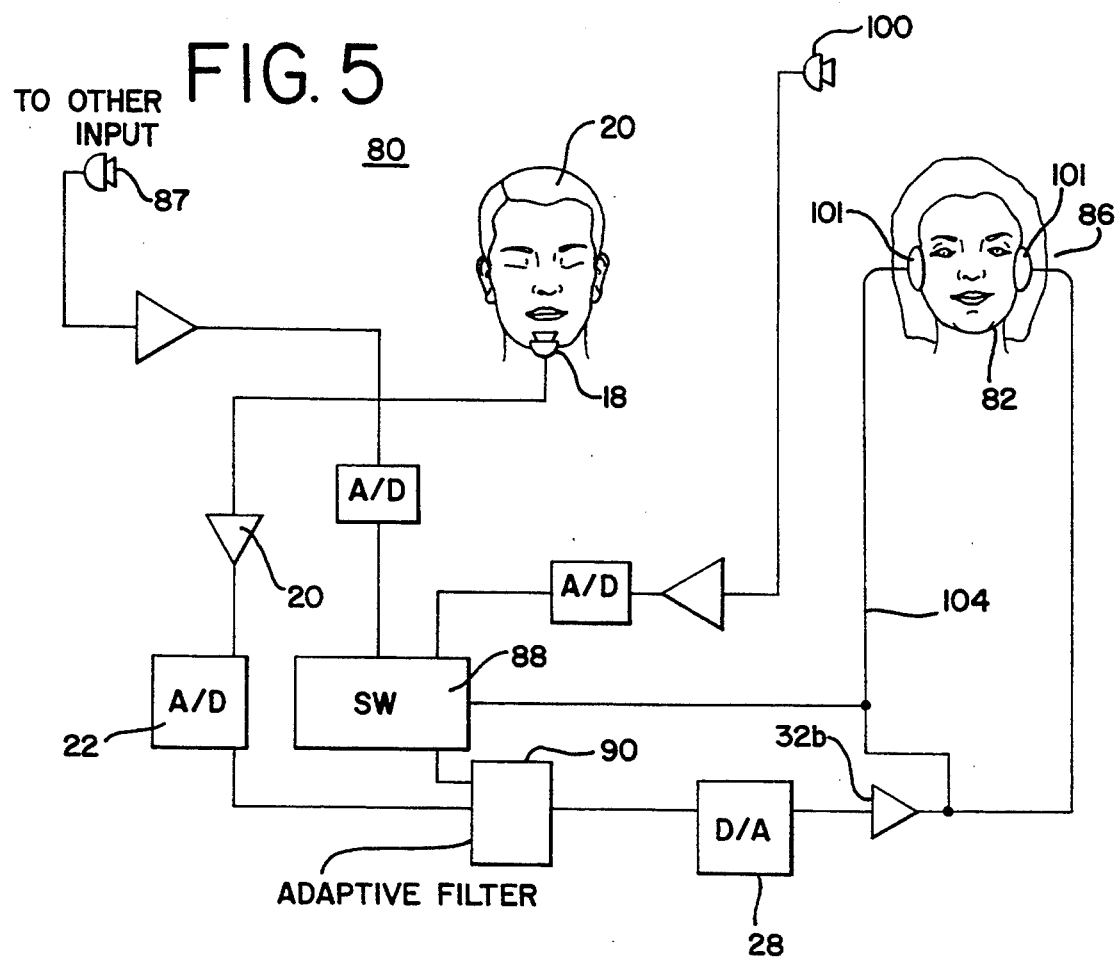
FIG. 5 depicts another embodiment of the invention for use by a non-snoring person, having a selection switch for selecting a plurality of input signals.

FIG. 5 discloses another embodiment of the invention wherein filter 90 is used to filter out the snore signal to the ear of an adjacent non-snoring individual 82. The system 80 allows a non-snoring person 82 or other individual other than the snoring person to select between various sound inputs such as ambient noise or input from another sound source.

Input from another sound source may be received from a microphone 87 which may be in another room of the house so that an alarm or other warning system may be heard. Another input may be a stereo input or other type of audio input. A switch 88 couples with the microphone 87 and the filter 90 which may be an adaptive filter, a fixed filter or any other suitable filter and is connected so that the microphone 87 may be switched directly to the earphone 86 so that the adjacent individual 82 may listen to some other audio input. When the switch 88 is switched to the snore filtering mode, the filter 90 serves to filter out the snoring noise.

Figure 6:
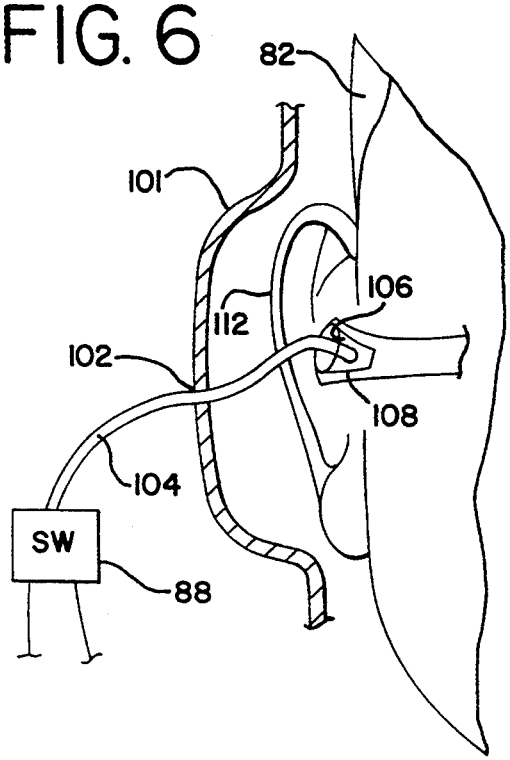
FIG. 6 is a partial cross-sectional view generally depicting an ear cover and audio tube combination in accordance with the embodiment shown in FIG. 5.

Referring to FIGS. 5 and 6, the earphones 86 also include a cover 101 for encapsulating an ear 112 and provides an acoustical seal about the ear. The cover 101 includes a channel 102 through which a sound tube 104 may be inserted. The sound tube 104 may have a plug 106 positioned on a distal end thereof. The plug 106 includes a channel 108 for receiving the sound tube 104. The switch 88 may be used to switch in outside audible sounds from other rooms or may be used to switch in sounds from the room which may include snoring sounds. The filter 90 may filter out the snoring and pass all other sound so that the wearer of the cover 101 will only hear non-snore sounds.

Figure 7:
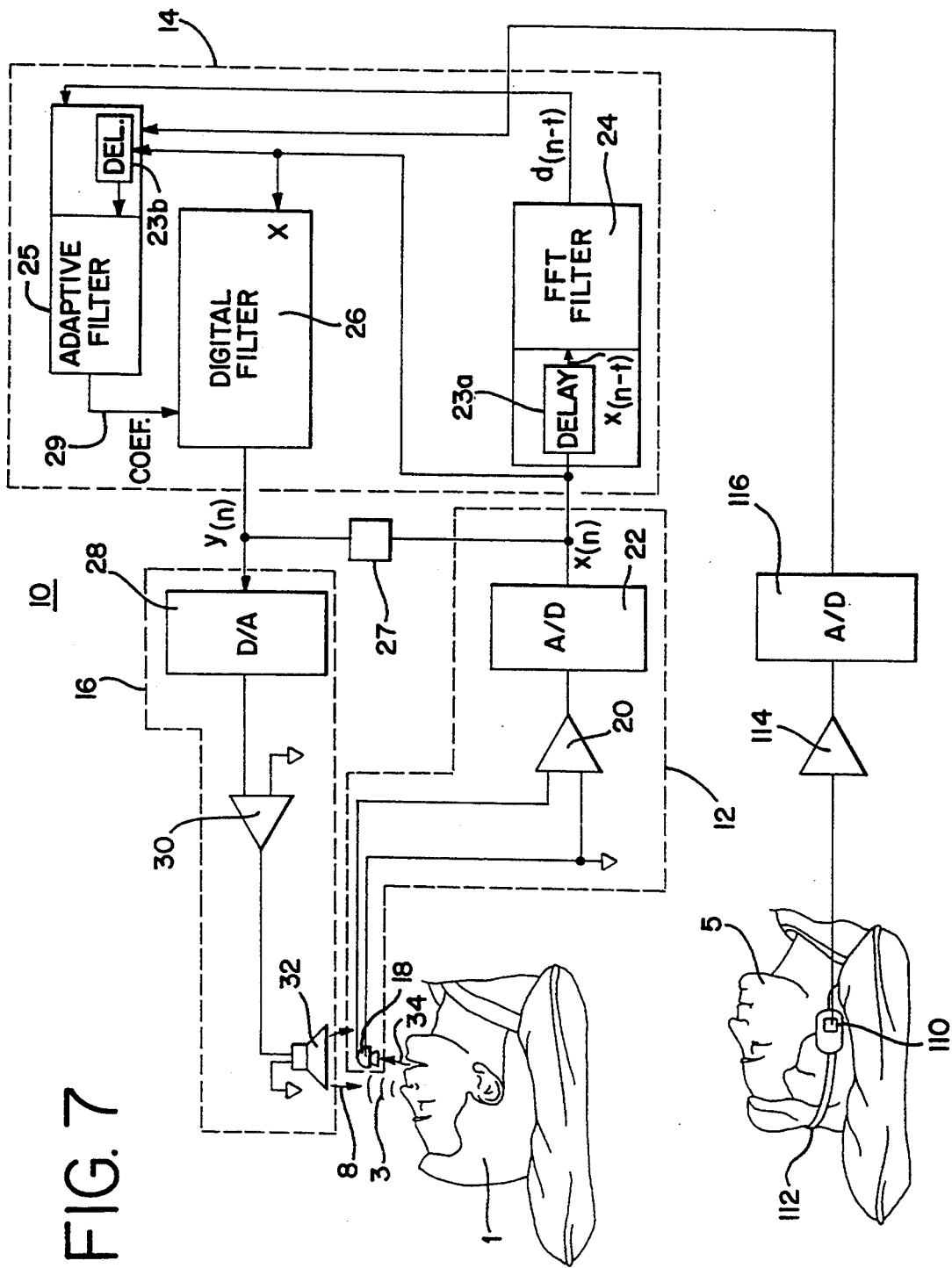
FIG. 7 schematically depicts another embodiment of the invention wherein a second microphone is used to detect resultant signal suppression which may be used as feedback information for the snore suppression system.

FIG. 7 depicts the system of FIG. 2 with the addition of a microphone 110 located in a headset 112 on an adjacent person 5 and positioned to receive a suppressed snore signal. The microphone 110 receives the suppressed snore signal as it is heard by the person 5. The received suppressed signal serves as feedback or an error signal to the system 10 so that the system may evaluate the effectiveness of the suppression and also adjust the snore canceling signal 8 to optimize effectiveness.

The microphone may be connected to an amplifier 114 similar to amplifiers 20 and 30. An A/D converting circuit 116 converts the analog received suppression signal to a digital signal. The digital suppressed signal serves as input to the adaptive filter 25. The adaptive filter 25 may use the suppressed signal to correct the coefficients 29 to better suppress the snore signal 3. The microphone may also be positioned anywhere in the room or at the plane of emission of the speaker.

In yet another embodiment, the distance between the transducing device and the snore source may be minimized by the use of a sound waveguide. For example, a sound waveguide may be attached to the speaker so that the plane of emission of the speaker is closer to the mouth of the snoring person.

Specific embodiments of a novel system for snoring suppression has been described for the purposes of illustrating the manner in which the invention may be used and made. It should be understood that the implementation of other variations and modifications of the invention in its various aspects will be apparent to those skilled in the art, and that the invention is not limited by the specific embodiments described. It is therefore contemplated to cover by the present invention any and all modifications, variations, or equivalents that fall within the true spirit and scope of the basic underlying principles disclosed and claimed herein.

What is claimed is:

1. A system for globally suppressing snoring signals generated from a snore sound source wherein a snoring sound signal has a phase angle and amplitude associated therewith, the system comprising:
   means, proximate the snore sound source, for receiving the snoring sound signal;
   sound transducing means proximate the snore sound source for directing a snore cancelling signal toward the snoring sound source to form a doublet between said sound transducing means and the snore sound source; and
   means, operatively coupled to said receiving means and to said sound transducing means, for generating said snore cancelling signal based on said received snore signal, such that said snore cancelling signal, as measured at a plane of emission of said sound transducing means, has approximately an 180 degree phase difference from the snoring signal phase angle and a substantially same amplitude as the snoring signal amplitude as measured at the sound source.

2. The system of claim 1 further comprising means, operatively coupled to said sound transducing means, for determining a position of said snore sound source when said snore sound source moves.

3. The system of claim 2 wherein said determining means includes means for preventing said canceling signal from being output by said transducing means in response to a determined position of said sound source.

4. The system of claim 2 wherein said determining means includes:
   a position sensor operatively coupled to detect a position of said sound source; and
   control means, operatively coupled to said position sensor, for activating or deactivating said transducing means in response to a signal output from said position sensor.

5. The system of claim 1 further including transducer control means, operatively coupled to said sound transducing means and to said receiving means, for preventing said canceling signal from being output by said transducing means when the snoring signal, as received by said receiving means, is not within predetermined signal criteria.

6. The system of claim 1 further including transducer control means, operatively coupled to said transducer means and said generating means, and wherein said generating means includes an adaptive filtering stage that determines whether the adaptive filtering stage is unstable, such that said transducer control means prevents said canceling signal from being output by said transducing means when the adaptive filter is unstable.

7. The system of claim 1 wherein said receiving means includes analog to digital conversion means for converting at least a portion of the received snore signal to a digital signal representation; and said generating means is comprised of digital signal processing means, adapted to receive said digital signal representation, for determining a plurality of filter coefficients and for modifying said digital signal representation using said coefficients to generate a pre-output canceling signal such that said pre-output canceling signal becomes said canceling signal when output by said transducing means.

8. The system of claim 7 wherein said digital signal processing means further includes filter means for splitting said digital signal representation into a plurality of frequency ranges.

9. The system of claim 1 wherein said means for receiving comprises a cordless microphone coupled to a mouthpiece worn by a snoring person.

10. The system of claim 1 further comprising another receiving means for receiving a suppressed snore signal where said received suppressed snore signal is input to said cancel signal generating means to effectuate evaluation of the effectiveness of snore signal suppression.

11. The system of claim 2 further comprising means for receiving an output signal from said position determining means and for maintaining a relative position between said transducing means and said snore sound source.

12. A system for globally suppressing snoring signals generated from a snore sound source wherein a snoring sound signal has a phase angle and amplitude associated therewith, the system comprising:

means, proximate the snore sound source, for receiving the snoring sound signal;

sound transducing means proximate the snore sound source for directing a snore cancelling signal toward the snoring sound source to form a doublet between said sound transducing means and the snore sound source;

means, operatively coupled to said receiving means and to said sound transducing means, for generating said snore cancelling signal based on said received snore signal, such that said snore cancelling signal, as measured at a plane of emission of said sound transducing means, has approximately an 180 degree phase difference from the snoring signal phase angle and a substantially same amplitude as the snoring signal amplitude as measured at the snore source;

means, operatively coupled to said sound transducing means, for determining a position of said snore sound source; and transducer control means, operatively coupled to said sound transducing means and to said receiving means for preventing said cancelling signal from being output by said transducing means when the snoring signal, as received by said receiving means, is not within predetermined signal criteria.

13. The system of claim 12 wherein said position determining means includes:

a position sensor operatively coupled to detect a position of said sound source; and control means, operatively coupled to said position sensor, for activating or deactivating said transducing means in response to a signal output from said position sensor.

14. The system of claim 13 wherein said receiving means includes analog to digital conversion means for converting at least a portion of the received snore signal to a digital signal representation; and said generating means further comprises digital signal processing means, adapted to receive said digital signal representation, for determining a plurality of filter coefficients and for modifying said digital signal representation using said coefficients to generate a pre-output canceling signal such that said pre-output cancelling signal becomes said canceling signal when output by said transducing means.

15. The system of claim 14 wherein said digital signal processing means further includes filter means for splitting said digital signal representation into a plurality of frequency ranges.

16. The system of claim 12 wherein said sound transducing means is comprised of a plurality of speakers and said system further comprises means for selectively allowing at least one of the plurality of speakers to output said cancel signal in response to an output signal from said position determining means.

17. The system of claim 13 wherein said means for receiving comprises a cordless microphone coupled to a mouthpiece worn by a snoring person.

18. A method for globally suppressing snoring signals generated from a snore sound source wherein a snoring sound signal has a phase angle and amplitude associated therewith, the method comprising:

receiving the snoring sound signal proximate the snore sound source;

directing a snore canceling signal from a sound transducer proximate the snore sound source toward the snoring sound source to form a doublet between said sound transducing means and the snore sound source; and generating said snore canceling signal based on said received snore signal, such that said snore canceling signal, as measured at a plane of emission of said sound transducing means, has approximately an 180 degree phase difference from the snoring signal phase angle and a substantially same amplitude as the snoring signal amplitude as measured at the snore source.

19. The method of claim 18 further comprising the step of: preventing said canceling signal from being output by said transducing means when the snoring signal, as received by said receiving means, is not within predetermined signal criteria.

20. A method for globally suppressing snoring signals generated from a snore sound source wherein a snoring sound signal has a phase angle and amplitude associated therewith, the method comprising the steps of:

receiving the snoring sound signal proximate the snore sound source;

directing a snore canceling signal from a sound transducer proximate the snore sound source toward the snoring sound source to form a doublet between said sound transducing means and the snore sound source;

generating said snore canceling signal based on said received snore signal, such that said snore canceling signal, as measured at a plane of emission of said sound transducing means, has approximately an 180 degree phase difference from the snoring signal phase angle and a substantially same amplitude as the snoring signal amplitude as measured at the snore source;

determining a position of said snore sound source during movement of said snore sound source; and preventing said canceling signal from being output by said transducing means when the snoring signal, as received by said receiving means, is not within predetermined signal criteria.

* * * * *